United States Patent
Fischer et al.

(10) Patent No.: US 10,576,088 B2
(45) Date of Patent: Mar. 3, 2020

(54) COMPOSITIONS COMPRISING FINAFLOXACIN AND TRIS

(71) Applicant: MerLion Pharmaceuticals Pte. Ltd., Singapore (SG)

(72) Inventors: Carsten Fischer, Berlin (DE); Andreas Vente, Berlin (DE); Sven-Eric Wohlert, Berlin (DE)

(73) Assignee: MerLion Pharmaceuticals Pte. Ltd., Singapore (SG)

( * ) Notice: Subject to any disclaimer, the term of this patent is extended or adjusted under 35 U.S.C. 154(b) by 0 days.

(21) Appl. No.: 15/523,680

(22) PCT Filed: Oct. 9, 2015

(86) PCT No.: PCT/IB2015/057729
§ 371 (c)(1),
(2) Date: May 2, 2017

(87) PCT Pub. No.: WO2016/071784
PCT Pub. Date: May 12, 2016

(65) Prior Publication Data
US 2017/0326151 A1    Nov. 16, 2017

(30) Foreign Application Priority Data

Nov. 3, 2014 (DE) .................. 10 2014 115 951

(51) Int. Cl.
| | | |
|---|---|---|
| *A61K 31/5383* | (2006.01) | |
| *A61K 9/00* | (2006.01) | |
| *A61K 47/02* | (2006.01) | |
| *A61K 47/18* | (2017.01) | |
| *A61K 9/08* | (2006.01) | |

(52) U.S. Cl.
CPC ........ *A61K 31/5383* (2013.01); *A61K 9/0019* (2013.01); *A61K 9/08* (2013.01); *A61K 47/02* (2013.01); *A61K 47/18* (2013.01)

(58) Field of Classification Search
CPC . A01N 47/02; A01N 47/56; A01P 7/04; A01P 7/00; A01C 1/06; A61P 33/00; A61K 31/415; C07D 231/44
USPC .................. 504/100; 514/404; 548/369.1
See application file for complete search history.

(56) References Cited

U.S. PATENT DOCUMENTS

| | | |
|---|---|---|
| 6,133,260 A | 10/2000 | Matzke et al. |
| 8,536,167 B2 | 9/2013 | Stroman et al. |
| 2004/0127537 A1* | 7/2004 | Gokarn ............... A61K 9/0014 |
| | | 514/406 |
| 2014/0162990 A1 | 6/2014 | Boudreaux et al. |

FOREIGN PATENT DOCUMENTS

WO    2014/165660 A1    10/2014

OTHER PUBLICATIONS

Strickley, "Solubilizing Excipients in Oral and Injectable Formulations," Pharmaceutical Research, vol. 21, No. 2, Feb. 2004, pp. 201-230. (Year: 2004).*
Sakr et al., "Novel Antimicrobial Agents: A Review," International Journal of Pharmacy & Technology, Mar. 2014, vol. 5, Issue No. 4, 2824-2838. (Year: 2014).*
International Search Report for corresponding PCT/IB2015/057729 dated Jan. 4, 2016, four pages.
"Finafloxacin," http://www.merlionpharma.com/?q=node/16, 2009, three pages.
Lemaire et al., "Activity of finafloxacin, a novel fluoroquinolone with increased activity at acid pH, towards extracellular and intracellular Staphylococcus aureus, Listeria monocytogenes and Legionella pneumophila," International Journal of Antimicrobial Agents 38 (2011) pp. 52-59.
Van Bambeke, "Renaissance of antibiotics against difficult infections: Focus on oritavancin and new ketolides and quinolones," Annals of Medicine, 46, 2014, pp. 512-529.
Pucci et al., "Investigational Antimicrobial Agents of 2013," Clinical Microbiology Reviews, Oct. 2013, vol. 26, No. 4, pp. 792-821.

* cited by examiner

*Primary Examiner* — Aradhana Sasan
(74) *Attorney, Agent, or Firm* — Rankin, Hill & Clark LLP

(57) ABSTRACT

It was found that finafloxacin has a high solubility in the presence of Tris. Such solubility is significantly higher than in the presence of other compounds typically used as buffers (e.g. phosphate buffer). The observed significant increase in solubility of finafloxacin in compositions comprising Tris is further advantageously accompanied by a long term stability of such solutions. Tris is therefore to be regarded as a specific tool to considerably enhance the solubility of finafloxacin in solutions. By preparing compositions comprising Tris it is possible to dissolve finafloxacin in such an amount therein that these compositions can effectively be used as parenteral compositions for the treatment of bacterial infections.

11 Claims, No Drawings

COMPOSITIONS COMPRISING FINAFLOXACIN AND TRIS

BACKGROUND OF THE INVENTION

The present invention relates to compositions comprising finafloxacin and Tris. Such compositions may represent pharmaceutically acceptable parenteral compositions and can be used for the treatment of bacterial infections such as urinary tract infections, intra-abdominal infections, skin and soft tissue infections, diabetic foot infections, bacteremia, and respiratory tract infections.

Finafloxacin (INN International Nonproprietary name) is an antibiotic of the class of the quinolone carboxylic acids of the following formula: (−)-8-cyano-1-cyclopropyl-6-fluoro-7-[(4aS,7aS)-hexahydropyrrolo[3,4-b]-1,4-oxazin-6(2H)-yl]-4-oxo-1,4-dihydroquinoline-3-carboxylic acid. Finafloxacin and derivatives thereof can be synthesized according to the methods described in WO 98/26779 by Matzke et al., the contents of which are herein incorporated by reference in their entirety. Finafloxacin has been described as useful in the treatment of *H. pylori* infections (EP0946176) or of ophthalmic, otic, or nasal infections (U.S. Pat. No. 8,536,167).

WO 98/26779, EP0946176 or U.S. Pat. No. 8,536,167 do not describe any pharmaceutical preparations which are suitable for the parenteral administration. Parenteral administration of drugs is especially crucial for the treatment of intensive care patients which are often not able to take oral medication but it can also help to quickly reduce the number of pathogens in an infection site due to the rapid delivery of the drug into the blood stream.

For a parenteral use, finafloxacin must be formulated as a stable, efficacious composition comprising a pharmaceutically sufficient amount of the active ingredient in an acceptable small volume in order to be usable as a parenteral application, i.e. relatively high concentrations of finafloxacin dissolved reliably and stable. The degradation of the active pharmaceutical ingredient or an excipient must be avoided when stored for a period of time.

It is known that the solubility characteristics are a general problem by using and handling finafloxacin. The solubility of finafloxacin is regarded to be not sufficient to generate physically stable solutions of high enough concentration at acceptable pH values to effectively treat infections in physiological solvents. The instability manifests itself by the formation of sub-visible and visible particles during storage. In addition, due to the poor solubility of finafloxacin there is the problem of administering a composition containing, e.g., 200 mg to 1000 mg or more of the active compound in an acceptable volume of parenteral applicable solution.

Thus, there is the need for compositions containing sufficient amounts of finafloxacin in acceptable volumes, and having also long term stability characteristics so such compositions can be used as pharmaceutically parenteral compositions.

SHORT DESCRIPTION OF THE INVENTION

Surprisingly, it was found that finafloxacin has a high solubility in the presence of Tris. Such solubility is significantly higher than in the presence of other substances typically used as buffers (e.g. phosphate buffer). The observed significant increase in solubility of finafloxacin in compositions comprising Tris is further advantageously accompanied by a long term stability of such solutions. Both effects lead to a completely unexpected result. Tris is therefore to be regarded as a specific tool to considerably enhance the solubility of finafloxacin in solutions. By preparing compositions comprising Tris it is possible to dissolve finafloxacin stably in such an amount therein that these compositions can effectively be used as parenteral compositions for the treatment of bacterial infections. Suitable compositions according to the invention comprise 1 to 6 g/l finafloxacin, 7 to 8 g/l NaCl, 1 to 2 g/l Tris and having a pH of 8.0 to 8.5. A specific composition according to the invention is for example a composition comprising 3.2 g/l finafloxacin, 7.8 g/l NaCl, 1.21 g/l Tris and having a pH of 8.25.

DETAILED DESCRIPTION OF THE INVENTION

The compositions of the present invention comprise finafloxacin and Tris. Tris is the abbreviation for 2-amino-2-hydroxymethyl-propane-1,3-diol or tris(hydroxymethyl)aminomethane. Another abbreviation for Tris is also THAM. The chemical formula is $(HOCH_2)_3CNH_2$. Tris is known as one of the mostly commonly used buffers used in biochemistry and molecular biology. The effective buffer range is between 7 and 9 and thus meets the typical physiological pH of most living organisms. A common form of Tris is Tris hydrochloride (Tris HCl). At higher concentrations Tris itself is used as an alternative to sodium bicarbonate as medication against hyperacidity.

The term "Tris" in connection with the compositions according to the invention is intended to encompass all chemical forms of Tris, including without limitation the free base, the conjugate acid (Tris HCl), any Tris salts and any derivatives of Tris, as well as any other compounds having the same or similar mode of action in the alkaline pH range as Tris as specified and claimed in connection with the compositions of the present invention.

Comparisons with other buffers, for example phosphate, or with a pH adjusted solution in water for injection (WfI) showed that Tris increases the solubility of finafloxacin significantly. This result surprisingly indicates that Tris itself has a remarkable solubilizing effect. This effect is new and independent from the ability of Tris to buffer a solution. A further advantage is that use of Tris prevents a pH drop, during storage or when diluted with isotonic sodium chloride (NaCl) for example, due to its buffer capacity in the alkaline pH range. A preferred composition according to the invention has a pH of 8.0 to 8.5.

The compositions according to the invention may contain Tris concentrations within the range of about 0.001 M and 0.2 M, preferably the concentration is of 0.002 M to 0.1 M. A suitable composition according to the invention has for example a Tris concentration of 0.01 M. The use of close to equimolar amounts of Tris and finafloxacin in the compositions according to the invention is preferred.

By using Tris within the above identified concentrations and pH ranges as one component in the compositions according to the invention it is possible to prepare pharmaceutically acceptable parenteral compositions. Due to the improved solubility in Tris comprising compositions finafloxacin concentrations of pharmaceutically sufficient level can be obtained. The phrase "pharmaceutically acceptable" is art-recognized and refers to compositions, polymers and other materials and/or dosage forms which are suitable for use in contact with the tissues of human beings and animals without excessive toxicity, irritation, allergic response, or other problem or complications, commensurate with a reasonable benefit/risk ratio as determined by one of ordinary skill in the art.

Embodiments of the compositions of the present invention comprise one or more vehicles or excipients. Vehicles/excipients commonly used in pharmaceutical compositions include, but are not limited to tonicity agents, preservatives, chelating agents, buffering agents, surfactants, antioxidants and radical scavengers. Other excipients comprise solubilizing agents, stabilizing agents, comfort-enhancing agents, polymers, emollients, pH-adjusting agents and/or lubricants. In preferred embodiments according to the present invention the concentrations of the excipient(s) are typically, from 0.1 to 100 times the concentration of finafloxacin and the excipient(s) are selected on the basis of their inertness towards finafloxacin. The amount of the excipients should be selected that preferably a tonicity of 200 to 700 mOsm/kg, more preferably of 260 to 390 mOsm/kg, is obtained. Examples for tonicity agents include, but are not limited to, NaCl, glucose, fructose, maltose, sorbitol, sucrose, xylitol, glycerol (glycerine/glycin), mannitol or mixtures of these.

A preferred salt within the compositions according to the invention is sodium chloride. NaCl concentrations from 0.4% to 1.0% (w/v) are suitable, particular preferably is a range of 0.6% to 0.9% (w/v) of sodium chloride, and preference is given to an amount of 0.7% to 0.8% (w/v) sodium chloride. In general, a range from 260 to 390 mOsmol/kg is considered to be isotonically suitable. Compositions according to the invention may comprise 7.8 g/l NaCl in order to obtain 280 mOsmol/kg.

The term "finafloxacin" in connection with the compositions according to the invention is intended to encompass finafloxacin HCl, finafloxacin free base, and other pharmaceutically acceptable salts, derivatives, enantiomers, or hydrates thereof. Diastereomerically and enantiomerically pure finafloxacin is preferred for use in embodiments of the present invention.

A preferred salt in certain embodiments of the compositions according to the present invention is finafloxacin monohydrochloride. However, pharmaceutically acceptable salts of finafloxacin can also be used, including, but not limited to, salts with pharmaceutically acceptable inorganic and organic acids such as acetic, lactic, succinic, maleic, malic, tartaric, citric, gluconic, ascorbic, benzoic, napthalene-1,5-disulfonic, napthalene-2-sulfonic, cinnamic, fumaric, dihydroxyfumaric, glutamic, oxaloacetic, glutaric, tartaric, salicylic, phosphoric, hydrochloric, hydrobromic, hydroiodic, sulfamic, pivalic, stearic, edisilic, isethionic, sulfuric, methanesulfonic, ethanesulfonic, benzenesulfonic, toluenesulfonic and sulfonic acid and the like. Suitable salts are furthermore those of inorganic or organic bases, such as KOH, NaOH, $Ca(OH)_2$, $Al(OH)_3$, piperidine, morpholine, ethylamine, triethylamine arginine and the like. Included within the scope of the invention are the hydrated forms of the compounds that contain various amounts of water or as solvates with other solvent molecules. Non-limiting examples of hydrates include monohydrates, dihydrates, etc. Non-limiting examples of solvates include ethanol solvates, acetone solvates, etc.

Pharmaceutically acceptable compositions according to the invention comprise finafloxacin at a concentration of 0.2 g/l to 50 g/l, preferably at a concentration of 0.4 g/l to 25 g/l mg, most preferably at a concentration of 0.8 g/l to 13 g/l. Preferred embodiments of the invention are compositions that comprise 1 to 6 g/l finafloxacin, 7 to 8 g/l NaCl, 1.0 to 2 g/l Tris. A specific composition according to the invention is for example a composition comprising 3.2 g/l finafloxacin, 7.8 g/l NaCl, 1.21 g/l Tris. Such compositions have preferably a pH of about 8.0 to 8.5 and especially a pH of 8.25.

In particular embodiments, the compositions of the present invention are administered once a day. However, the compositions of the present invention may also be formulated for administration at any other frequency of administration, including two times a day, three times a day, every two days or any greater or lesser frequency, at regular or irregular intervals, changing or consistent. Such dosing frequency is also maintained for a varying duration of time depending on the therapeutic regiment. The duration of a particular therapeutic regimen may vary from one-time dosing to a regiment that extends for days, weeks or months. One of ordinary skill in the art would be familiar with determining a therapeutic regiment for a specific indication that incorporates a pharmaceutically effective amount of finafloxacin or a composition thereof. The phrase "pharmaceutically effective amount" is an art-recognized term, and refers to an amount of an agent that, when incorporated into a pharmaceutical composition of the present invention, produces some desired effect at a reasonable benefit/risk ration applicable to any medical treatment. The effective amount may vary depending on such factors as the disease or infectious agent being treated, the particular composition being administered, or the severity of the disease or pathogen.

The compositions of the invention are particularly directed toward treating mammalian and human subjects having or at risk of having a microbial infection. Certain embodiments of the present invention may also preferably be used prophylactically to prevent infection by an infectious agent. The compositions according to the invention can effectively be used for the treatment of bacterial infections such as urinary tract infections, intra-abdominal infections, skin and soft tissue infections, diabetic foot infections, bacteremia, prostatitis, bone and joint infections, respiratory tract infections, etc.

The compositions according to the invention may be prepared by conventional methods of preparing aqueous pharmaceutical compositions known to those of skill in the art. The administration of embodiments of such compositions for the treatment of bacterial infections or for the prophylactic use to prevent infection in mammalian and human subjects can be by a number of methods known to someone of ordinary skill in the art.

EXAMPLES

Example 1: Solubility of Finafloxacin HCl

The solubility of finafloxacin, in form of its monohydrochloride salt, was tested at pH values between 7.3 and 9.0, using the following solutions:

0.01 M Tris: Water for injection 800 ml, Tris 1.21 g, sodium chloride 7.5 g, water for injection ad 1000 ml; pH was adjusted with HCl/NaOH.

0.025 M Phosphate: Water for injection 800 ml, sodium dihydrogen phosphate 1.950 g, disodium hydrogen phosphate 2.225 g, sodium chloride 7.5 g, water for injection ad 1000 ml; pH was adjusted with HCl/NaOH.

WfI: Water for injection 900 ml, sodium chloride 7.5 g, water for injection ad 1000 ml; pH was adjusted with HCl/NaOH.

Finafloxacin HCl was added stepwise to 100 ml of the aqueous solutions, re-adjusting the pH subsequently until the added finafloxacin HCl did not dissolve anymore.

|  | pH 7.5 | pH 8.0 | pH 8.5 | pH 9.0 |
|---|---|---|---|---|
| 0.01M Tris | 6.0 mg/ml | 15.0 mg/ml | >28 mg/ml | >28 mg/ml |
| 0.025M Phosphate | 2.0 mg/ml | 4.0 mg/ml | 6.0 mg/ml | 8.0 mg/ml |
| pH-adjusted WfI | 2.0 mg/ml | 4.0 mg/ml] | 6.0 mg/ml | 6.0 mg/ml |

The results of example 1 clearly demonstrate the significantly improved solubility of finafloxacin in Tris. While the solubility in WfI and phosphate buffer was comparably low, the use of 0.01 M Tris revealed a 3-4-fold increase in solubility. The results further show that the solubility of finafloxacin is pH dependent.

Example 2: Solubility of Finafloxacin HCl in Different Concentrations of Tris Solutions 0.25 M Tris: Water for injection 800 ml, Tris 30.3 g, sodium chloride 7.5 g, water for injection ad 1000 ml; pH was adjusted with HCl/NaOH.

0.17 M Tris: Water for injection 800 ml, Tris 20.0 g, sodium chloride 7.5 g, water for injection ad 1000 ml; pH was adjusted with HCl/NaOH.

0.08 M Tris: Water for injection 800 ml, Tris 10.0 g, sodium chloride 7.5 g, water for injection ad 1000 ml; pH was adjusted with HCl/NaOH.

Finafloxacin HCl was added stepwise to 100 ml of the aqueous solutions until the added finafloxacin HCl did not dissolve anymore. In contrast to example 1 the pH was not re-adjusted after the stepwise addition of finafloxacin.

|  | 0.08M TRIS | 0.17M TRIS | 0.25M TRIS |
|---|---|---|---|
| pH 7.0 | 0 mg/ml | 0 mg/ml | 0 mg/ml |
| pH 7.4 | 0 mg/ml | 2.0 mg/ml | 2.0 mg/ml |
| pH 7.8 | 4.0 mg/ml | 6.0 mg/ml | 8.0 mg/ml |
| pH 8.2 | 6.0 mg/ml | 10.0 mg/ml | 15.0 mg/ml |
| pH 8.6 | 9.0 mg/ml | 19.0 mg/ml | 24.0 mg/ml |
| pH 9.0 | 10.0 mg/ml | 23.0 mg/ml | 28.0 mg/ml |

The results reveal that the solubility of finafloxacin is dependent from the Tris concentration. The above results show generally a lower solubility of finafloxacin than in example 1 as the pH was not readjusted after the stepwise addition of finafloxacin.

Example 3: Stability of Finafloxacin Compositions Comprising Tris

The following composition was used to test the stability:

| Component | Quantity (g per liter) | Function |
|---|---|---|
| Finafloxacin | 3.20 | active ingredient |
| NaCl | 7.80 | vehicle |
| Tris | 1.21 | solubility enhancing agent |
| NaOH 1M (for pH adjustment to 8.25) | q.s. | pH adjustment |
| HCl 1M (for pH adjustment to 8.25) | q.s. | pH adjustment |
| Water for injection | add to 1.00 L | solvent | q.s quantum satis means to use "as much as necessary" of the substance

Solutions prepared according to this formulation showed a long term stability of at least 24 months.

Example 4 Efficacy of Finafloxacin Compositions Comprising Tris

The efficacy of finafloxacin compositions including Tris between pH 8.0-8.5 was examined and determined as follows:

4.1 Bacteria were incubated in a finafloxacin composition at pH 8.0 containing 0.05 M Tris and the minimal inhibitory concentration (MIC) of finafloxacin, defined as the minimal finafloxacin concentration that inhibited the growth of the bacterium, was determined using a standard in vitro susceptibility test. The MIC for *S. aureus* 29213 was 0.5 µg/ml, the MIC for *E. coli* 25922 was 0.25 µg/ml.

4.2 Mice were infected with $3.9 \times 10^5$ *E. coli* ATCC 25922 suspended in 1% porcine mucin administered by a 0.5 ml intraperitoneal injection. Antibacterial treatment with a finafloxacin composition comprising 0.01 M Tris was initiated 4 hours post infection with a second dose 12 hours post infection. The bacterial burden in the peritoneal fluid and blood culture was determined 24 hours post infection. Finafloxacin was effective at all doses with 1 mg/kg causing a reduction in burden of 3.1 log 10 cfu/g, finafloxacin administered at 3, 10 and 30 mg/kg were increasingly effective causing reductions of 4.4, 5.0 and 6.5 log 10 cfu/g, respectively.

4.3 Patients with complicated urinary tract infections and pyelonephritis were treated with an intravenous dose of 800 mg Finafloxacin once daily. 17 days after the start of the treatment the microbiological cure results were determined. Microbiological cure is defined as the reduction of the concentration of the pathogen in the urine to a titer of $\leq 10^3$ cfu/ml. The finafloxacin composition comprising 0.01 M Tris caused an efficient eradication of the pathogens. The microbiological cure rate was 83%.

Example 5 Safety of Finafloxacin Compositions Comprising Tris

Intravenous administration of Finafloxacin to rats for 2 weeks at dose levels of 60, 120 and 200 mg/kg/day was generally well tolerated during the in-life toxicological appraisal. The test article was formulated in 0.01 M Tris containing sodium chloride to 0.75% (w/v), adjusted in water for injection to pH 8.5.

The invention claimed is:

1. A parenteral composition for intravenous administration, comprising:
   finafloxacin at a concentration of 0.4 g/l to 25 g/l;
   a solubilizer, which is Tris at a concentration of 0.001 M to 0.1 M;
   a tonicity agent in an amount to adjust the tonicity of the composition to 200 to 700 mOsm/kg; and
   water;
   wherein the parenteral composition has a pH of 8.00 to 10.00 and a tonicity of 200 to 700 mOsm/kg.

2. The parenteral composition for intravenous administration according to claim 1, said composition comprising Tris at a concentration of 0.002 M to 0.1 M.

3. The parenteral composition for intravenous administration according to claim 1, said composition further comprising one or more pharmaceutical excipients.

4. The parenteral composition for intravenous administration according to claim 1, wherein the tonicity agent is sodium chloride, and is present in the parenteral composition at a concentration of 0.4% to 1.0% (w/v).

5. The parenteral composition for intravenous administration according to claim 1, wherein said composition comprises 1.6 to 6.4 g/l finafloxacin, 7 to 8 g/l NaCl, and 1 to 2 g/l Tris, and said composition has a pH of 8.0 to 8.5.

6. A parenteral composition for intravenous administration consisting of:
   finafloxacin at a concentration of 0.4 g/l to 25 g/l;
   a solubilizer, which is Tris, at a concentration of 0.002 M to 0.1 M;
   a tonicity agent, which is sodium chloride, at a concentration of 0.4% to 1.0% (w/v); and
   water;
   wherein said parenteral composition for intravenous administration has a pH of 8 to 10, and a tonicity of 260 to 390 mOsm/kg.

7. A parenteral composition for intravenous administration consisting of:
   finafloxacin at a concentration of 1.6 g/l to 6.4 g/l;
   a solubilizer, which is Tris, at a concentration of 0.002 M to 0.1 M
   a tonicity agent, which is sodium chloride, at a concentration of 0.6% to 0.9% (w/v); and
   water;
   wherein said parenteral composition for intravenous administration has a pH of 8 to 8.5, and a tonicity of 270 to 350 mOsm/kg.

8. The parenteral composition for intravenous administration according to claim 1, said composition comprising 3.2 g/l finafloxacin, 7.8 g/l NaCl, 1.21 g/l Tris, and having a pH of 8.25.

9. The parenteral composition for intravenous administration according to claim 1, wherein a pH is in the range of 8.25 to 10.00.

10. The parenteral composition for intravenous administration according to claim 1, said composition consisting of 3.2 g/l finafloxacin, 7.8 g/l NaCl, 1.21 g/l Tris, and water, said parenteral composition for intravenous administration having a pH of 8.25.

11. The parenteral composition for intravenous administration according to claim 6, wherein the pH is in the range of 8.25 to 10.00.

* * * * *